(12) United States Patent
Faour et al.

(10) Patent No.: US 12,054,697 B2
(45) Date of Patent: Aug. 6, 2024

(54) HOP ACIDS FORMULATIONS AND METHODS

(71) Applicant: John I. Haas, Inc., Washington, DC (US)

(72) Inventors: Sami Faour, Washington, DC (US); Michail Karavolos, Great Malvern (GB); Guillermo Guerrero Vasquez, Great Malvern (GB)

(73) Assignee: John I. Haas, Inc., Washington, DC (US)

( * ) Notice: Subject to any disclaimer, the term of this patent is extended or adjusted under 35 U.S.C. 154(b) by 386 days.

(21) Appl. No.: 17/581,618

(22) Filed: Jan. 21, 2022

(65) Prior Publication Data

US 2022/0235298 A1 Jul. 28, 2022

Related U.S. Application Data

(60) Provisional application No. 63/140,712, filed on Jan. 22, 2021.

(51) Int. Cl.
*C12C 3/00* (2006.01)
*C12C 11/06* (2006.01)

(52) U.S. Cl.
CPC .............. *C12C 3/00* (2013.01); *C12C 11/06* (2013.01)

(58) Field of Classification Search
CPC ................................. C12C 3/00; C12C 11/06
See application file for complete search history.

(56) References Cited

U.S. PATENT DOCUMENTS

| | | | |
|---|---|---|---|
| 5,286,506 A | 2/1994 | Millis et al. | |
| 6,251,461 B1 | 6/2001 | Johnson et al. | |
| 6,893,857 B1 | 5/2005 | Maye et al. | |
| 8,778,646 B1 | 7/2014 | Chapman et al. | |
| 2017/0362496 A1* | 12/2017 | Emerstorfer | C09K 8/605 |
| 2018/0371307 A1* | 12/2018 | Emerstorfer | A01N 35/06 |

FOREIGN PATENT DOCUMENTS

| | | |
|---|---|---|
| EP | 0681029 B1 | 7/1997 |
| WO | 97/33971 A | 9/1997 |
| WO | 00/052212 A1 | 9/2000 |
| WO | 2004/072291 A2 | 8/2004 |
| WO | 2007/131669 A1 | 11/2007 |

OTHER PUBLICATIONS

International Search Report and Written Opinion, mailed Apr. 11, 2022, for International Application No. PCT/US2022/013341, 21 pages.

* cited by examiner

*Primary Examiner* — Anthony J Weier
(74) *Attorney, Agent, or Firm* — Seed IP Law Group LLP

(57) ABSTRACT

The present disclosure provides compositions and methods for improved hop acids formulations including myristic acid which have improved stability characteristics. The formulations may be used as an anti-bacterial agent in fermentation processes.

19 Claims, 12 Drawing Sheets

| Sample | Alpha acid extract with Myristic acid (%) | |
|---|---|---|
| | 5% | 10% |
| conditions | pH 12.06 | pH 12.73 |
| t=0, T=r.t. |  |  |
| t=24h, T=-2°C |  |  |
| Observation | Stable yellow solution | Stable yellow solution |

HOP ACIDS FORMULATIONS AND METHODS

TECHNICAL FIELD

The present disclosure relates generally to compositions and methods for improved hop acids formulations. More specifically, the disclosure relates to an improved formulation of hop derived alpha acids extracts comprising myristic acid and having improved stability characteristics.

BACKGROUND

Hops have been used in brewing for well over one thousand years. Hop cones contain lupulin glands that have two important bittering substances: alpha acids and beta acids. These acids are sometimes called humulones and lupulones, respectively. Hop acids were initially used as a preservative agent for beer prior to the existence of refrigeration. Today, they are primarily used to create the bitter taste and flavor of beer.

The term "hop acids," as used herein, means alpha acids, beta acids, mixtures of these acids, and/or other components found in hop extracts; for example, beta fraction, essential oils, waxes, and uncharacterized resins. The term "hop acids" also includes modified hop acids. Hop alpha acids consist of a mixture of analogues, including humulone, cohumulone, and adhumulone. Alpha acids make-up 10 to 15 percent w/w in dry hops and over 50 percent by weight of carbon dioxide hop extract. During the brewing of beer, hops are boiled and the alpha acids undergo thermal isomerization forming a new compound known as isoalpha acids. Isoalpha acids are the actual bittering and preserving compounds found in beer. Derivatives of isoalpha acids are made by performing simple chemical reductions. These reduced isoalpha acids include rhoisoalpha acids, tetrahydroisoalpha acids (THIAA), and hexahydroisoalpha acids (HHIAA) Thus the term "alpha acids" includes isoalpha acids, tetrahydroisoalpha acids, rhoisoalpha acids, and hexahydroisoalpha acids. Beta acids also consist of a mixture of analogues, including lupulone, colupulone, and adlupulone. The term "beta acids" also includes modified beta acids, such as hexa-hydro-beta acids.

Difficulty of maintaining a sterile condition free from bacteria is an important concern in conventional fermentation systems. The conditions used typically for fermentations in these systems are also conducive for bacterial growth. A single occurrence of contamination involves costly and time-consuming sterilization and loss of materials and production. The economics and efficiency of fermentation processes are frequently such that they cannot tolerate any such loss of production.

Current methods used to kill these unwanted microorganisms, among others, often involve introduction of foreign agents, such as antibiotics, heat, and strong chemical disinfectants, to the fermentation before or during production. Antibiotics and chemical disinfectants are expensive and can add greatly to the costs of large-scale production. Likewise, the use of heat requires substantial energy to heat the fermentation or yeast propagation vessels as well as, possibly requiring the use of special, pressure-rated vessels that can withstand the high temperatures and pressures generated in such heat sterilizing processes. Moreover, these chemicals are often hazardous materials requiring special handling and environmental and safety precautions, and are not "green", i.e., are not organic. Thus, existing methods of controlling growth of microorganisms add to the time and costs of production processes.

Aqueous formulations of hop alpha acids can be used as an anti-bacterial agent in fermentation processes and obviate the need for antibiotic or hazardous chemical use. Moreover, as a traditional component of beer for many centuries, hop acids are a proven organic consumable. Hops are one of the basic ingredients of beer and, as such, hops and hop extracts are considered GRAS (Generally Recognized as Safe) by the U.S. Food and Drug Administration (FDA).

Currently available formulations, however, form a resin precipitate when exposed to temperatures below 4° C. This separation/precipitation is not easily reversed upon return to normal room temperatures, making these formulations difficult to work with.

There is a need in the art for stable hop acid compositions for use in controlling, preventing, or reducing microorganism growth in processes utilizing fermentation in order to increase product yield without significant cost and time.

BRIEF SUMMARY

As described below, the present disclosure features compositions comprising hop acids and methods for utilizing these compositions, for example but not limited to, for reducing and/or preventing microorganism growth in processes utilizing fermentation, brewing, and distilling.

The present disclosure provides compositions comprising a hop derivative, myristic acid, and water. In certain embodiments, the hop derivative may comprise an alpha acid, beta acid, or a combination of alpha and beta acids. In some embodiments, the hop alpha acids or hop derived alpha acids may comprise reduced isoalpha acids. In some embodiments, the hop alpha acids or hop derived alpha acids may comprise reduced isoalpha acids including tetrahydroisoalpha acids (THIAA), hexahydroisoalpha acids (HHIAA), or a combination of tetrahydroisoalpha acids (THIAA) and hexahydroisoalpha acids (HHIAA). In another embodiment, the composition may further comprise hop beta acids or hop derived beta acids. In any of the previous embodiments, the composition is any one or more of a liquid, a powder, a colloid, an oil, and an emulsion.

In some embodiments, the hop alpha acids are present in an amount from about 1% to about 30% (w/w) and the myristic acid is present in an amount from about 0.05% to about 15% (w/v). In some embodiments, the hop alpha acids are present in an amount from about 1% to about 30% (w/w) and the myristic acid is present in an amount from about 0.2% to about 15% (w/v). In certain embodiments, the composition comprises hop alpha acids in an amount from about 1% to about 30% (w/w) and the myristic acid is present in an amount from about 0.05 to about 0.2% MA (w/v). In these embodiments, the composition does not form a precipitate when cooled to −8° C. and recovers its initial properties when warmed up to room temperature. In some embodiments, the composition comprises hop alpha acids in an amount from about 1% to about 30% (w/w) and the myristic acid is present in an amount from about from 0.3% to 1.5% MA (w/v). In these embodiments, the composition does not form a precipitate when the composition is cooled to −12° C. and recovers its initial properties when warmed up to room temperature. In certain embodiments, the composition comprises hop alpha acids in an amount from about 1% to about 30% (w/w) and the myristic acid is present in an amount from about from 0.3% to 0.4% MA (w/v). In these embodiments, the composition does not form a precipitate when cooled to −16.7° C. and recovers its initial properties when warmed up to room temperature.

In some embodiments, the hop alpha acids are present in an amount from about 1% to about 30% (w/w) and the myristic acid is present in an amount from about 0.25% to about 15% (w/v). In certain embodiments, the composition does not form a precipitate when cooled to 2° C. In some embodiments, a resin precipitates when the composition is cooled below −12° C. In further embodiments, a resin precipitates when the composition is cooled to −12° C. and resolubilizes when the composition is warmed to 20° C. and gently agitated.

The present disclosure further provides methods of controlling bacterial growth in a fermentation process, comprising adding a composition comprising hop alpha acids, myristic acid, and water to a fermentation vessel, a yeast propagation tank, or both. In some embodiments, the fermentation process is used for ethanol production. In certain embodiments, the fermentation process is used for yeast production. In a further embodiment, the method comprises adding an aqueous solution of a composition comprising hop alpha acids, myristic acid, and water to a process medium. The process medium can have a pH ranging from about 2 to about 6. Accordingly, a method is disclosed for controlling micro-organisms in an aqueous process medium comprising adding an effective amount of the compositions disclosed herein.

In certain embodiments, the disclosure provides a kit for reducing or preventing the growth of microorganisms comprising the compositions disclosed herein in a form suitable for delivery to a target site. In some embodiments, the target site is a fermentation vessel, a yeast propagation tank, or both. In certain embodiments, the target site is a heat exchanger, a liquefaction tank, or a seed tank.

Other features and advantages of the invention will be apparent from the detailed description, and from the claims.

BRIEF DESCRIPTION OF THE DRAWINGS

FIG. 1A shows the results for a formulation of 9% (w/w) hop beta acids and 10% (w/v) myristic acid ("beta-derived solution", second column), a formulation of 10% (w/w) hop alpha acids having pH 9.94 ("alpha derived solution", third column), and a formulation of 10% (w/w) hop alpha acids having pH 12.37 ("alpha derived solution", fourth column). FIG. 1B shows the results for two different formulations of 10% (w/w/) hop alpha acids with varying concentrations of myristic acid. The second column shows the results for a 5% (w/v) myristic acid formulation, and the third column shows the results for a 10% (w/v) myristic acid formulation.

FIG. 6A shows samples of a 20% (w/w/) hop alpha acids formulation with no myristic acid at room temperature (top left), at 2° C. (top right), at −12° C. (bottom left), after cooling to −12° C., rewarming to room temperature, and mixing (bottom center), and after cooling to −12° C., rewarming to room temperature, mixing, and standing at room temperature for three days (bottom right). FIG. 6B shows samples of a 20% (w/w) alpha acids formulation with 4% (w/v) myristic acid at room temperature (top left), at −10° C. (top center), after cooling to −10° C. and rewarming to room temperature (top right), at −12° C. (bottom left), after cooling to −12° C., rewarming to room temperature, and mixing (bottom center), and after cooling to −12° C., rewarming to room temperature, mixing, and standing at room temperature for three days (bottom right). FIG. 6C shows samples of a 20% (w/w) alpha acids formulation with 5% (w/v) myristic acid at room temperature (top left), at −11° C. (top center), after cooling to −11° C. and rewarming to room temperature (top right), at −12° C. (bottom left), after cooling to −12° C., rewarming to room temperature, and mixing (bottom center), and after cooling to −12° C., rewarming to room temperature, mixing, and standing at room temperature for three days (bottom right).

(FIG. 8B, top panel and FIG. 8C, top panel, respectively). Bottom panel for each formulation shows formulations rewarmed to room temperature from −12° C. All samples were rewarmed up to room temperature with gentle mixing by hand.

DETAILED DESCRIPTION

Figure 1A:
FIGS. 1A and 1B depict the results of cooling and rewarming several different hop acids formulations.

As described below, the present disclosure provides compositions comprising hop acids and/or their derivatives, and fatty acids. Upon exposure to low temperatures, aqueous hop alpha acid formulations form a resin precipitate and they freeze at temperatures lower than −11° C. Surprisingly, the present inventors have discovered that the addition of fatty acids to hop alpha acid formulations has several significant benefits. For example, the present inventors have discovered that the addition of myristic acid (MA), to an aqueous hop alpha acid formulation results in a stable solution that stays precipitate-free even when exposed to low temperatures, and has a lowered freezing temperature of −11° C. or −13° C. Further, in certain embodiments, when these compositions are cooled to −12° C. or −16° C. and rewarmed to room temperature with gentle mixing, the composition is clear and contains no resin or oily precipitate. These formulations are useful for inhibition, prevention, and/or control of bacterial growth in, for example but not limited to, fermentation processes for yeast production and ethanol production.

The present disclosure also provides compositions effective for reducing or preventing the growth of microorganisms. In certain embodiments, the present disclosure is directed to a process for controlling micro-organisms in an aqueous process medium comprising adding an effective amount of aqueous alkaline composition comprising hop acids and fatty acids to the process medium. Myristic acid has been previously added to hop beta acid formulations as an emulsifier, but it has been found that such formulations do not have lower freezing temperatures than hop beta acid formulations without myristic acid. Additionally, the addition of myristic acid to hop beta acid formulations does not prevent the appearance of precipitates when the compositions are cooled to −2° C. and re-warmed up to room temperature.

As used herein, the term "about," as applied to a numeric value or numerical range, means a value within +/−10% of the stated value.

As used herein, "room temperature" refers to the range of air temperatures that most people prefer for indoor settings when wearing typical indoor clothing. Room temperature is typically considered to be between about 20° C. and about 26° C.

As used herein, "an effective amount", means an amount effective in reducing, preventing, slowing the growth or proliferation of microorganisms.

As used herein, "hop alpha acids", or "hop derived alpha acids extract", or "alpha acids", refers to hop derived alpha acids and includes derivatives thereof, such as, isoalpha acids, reduced or modified isoalpha acids including tetrahydroisoalpha acids (THIAA), hexahydroisoalpha acids (HHIAA), rhoisoalpha acids, or combinations and mixtures thereof.

The compositions and/or formulations provided herein comprise hop alpha acids, fatty acids, and water. In certain embodiments, the hop acid is a natural hop acid or a derivative thereof, such as, alpha acid, beta acid, tetrahydroalpha acid (THAA), or hexahydrobeta acid (HHBA), or mixtures thereof; an isomerized hop acid or a derivative thereof, such as, isoalpha acid (IAA), rhoisoalpha acid (RIAA), tetrahydroisoalpha acid (THIAA) or hexahydroisoalpha acid (HHIAA) or mixtures thereof. Alpha acids contained in the hop acid may be transformed into isoalpha acids during the preparation of the hop acid solution and maintain their anti-bacterial/anti-microbial effect. The hop alpha acids or hop derived alpha acids may comprise hexahydroisoalpha acids and tetrahydroisoalpha acids. In any of the above embodiments, the hop alpha acids comprise hexahydroisoalpha acids and tetrahydroisoalpha acids at a ratio of about 1:1.

Depending on the hop acid product, the concentration of hop acids in the composition will vary. Generally, the final concentration of hop alpha acids ranges from about 1% to about 30% (w/w), in another aspect from about 5% to about 25% (w/w), an in another aspect from about 10% to about 20% (w/w). In certain embodiments, the hop alpha acids are present in the amount of about 10% (w/w). In some embodiments, the hop alpha acids are present in the amount of about 20% (w/w). Higher concentrations may be appropriate where longer transport times are required. Generally, hop acids in their acid form exhibit low solubility in water. However, hop acids can be mixed with an alkali metal hydroxide, for example potassium hydroxide, to make a water soluble alkali metal salt of the hop acids. Accordingly, it is advantageous to use alkali hydroxides, for example potassium hydroxide or sodium hydroxide or a mixture thereof as the alkaline medium to control micro-organisms. The concentrations of the alkaline medium ranges from about 20% to about 45 wt. %, or in another aspect from about 20 wt. %. In any of the previous embodiments, the hop alpha acids or hop derived alpha acids are in the form of potassium salts of isoalpha acids.

In any of the above embodiments, the fatty acids may be or may comprise myristic acid. Myristic acid is a saturated fatty acid with the molecular formula $CH_3(CH_2)_{12}COOH$, and the chemical name 1-tetradecanoic acid. Myristic acid has been previously added to hop beta acid formulations as an emulsifier, but it has been found that such formulations do not have lower freezing temperatures than hop beta acids formulations without myristic acid. Additionally, the addition of myristic acid to hop beta acids formulations does not prevent the appearance of precipitates when the compositions are cooled to −2° C. and re-warmed.

In some embodiments, the myristic acid is present in an amount from about 0.05% to about 15% (w/v), 0.25% to about 15% (w/v), from about 0.5% to about 10% (w/v), from about 1% to about 8% (w/v), or from about 2% to about 5% (w/v). In certain embodiments, the myristic acid is present in the amount of about 0.05% to 0.2% (w/v), 0.3% to about 1.5% (w/v), about 0.3% to about 0.4% (w/v). In further embodiments, the myristic acid is present in the amount of about 0.25% (w/v), about 0.5% (w/v), about 1% (w/v), about 2.5% (w/v), about 4% (w/v), or about 5% (w/v). In some embodiments, the compositions provided herein comprise about 15% (w/w) hop alpha acids and 0.05% (w/v) myristic acid, about 15% (w/w) hop alpha acids and 0.1% (w/v) myristic acid, about 15% (w/w) hop alpha acids and 0.2% (w/v) myristic acid, about 15% (w/w) hop alpha acids and 0.3% (w/v) myristic acid, and about 15% (w/w) hop alpha acids and 0.4% (w/v) myristic acid. In certain embodiments, the composition provided herein comprises about 15% (w/w) hop alpha acids and 0.5% (w/v) myristic acid, about 15% (w/w) hop alpha acids and 0.75% (w/v) myristic acid, about 15% (w/w) hop alpha acids and 1.0% (w/v) myristic acid, about 15% (w/w) hop alpha acids and 1.25% (w/v) myristic acid, about 15% (w/w) hop alpha acids and 1.5% (w/v) myristic acid.

In some embodiments, the composition provided herein comprises 10% (w/w) hop alpha acids and 0.05% (w/v) myristic acid, 10% (w/w) hop alpha acids and 0.25% (w/v) myristic acid, 10% (w/w) hop alpha acids and 0.3% (w/v) myristic acid, 10% (w/w) hop alpha acids and 0.5% (w/v) myristic acid, 10% (w/w) hop alpha acids and 0.75% (w/v) myristic acid, 10% (w/w) hop alpha acids and 1% (w/v) myristic acid, 10% (w/w) hop alpha acids and 1.25% (w/v) myristic acid, 10% (w/w) hop alpha acids and 1.5% (w/v) myristic acid, 10% (w/w) hop alpha acids and 2.5% (w/v) myristic acid, 10% (w/w) hop alpha acids and 4% (w/v) myristic acid, 10% (w/w) hop alpha acids and 5% (w/v) myristic acid, or 10% (w/w) hop alpha acids and 10% (w/v) myristic acid. In further embodiments, the compositions provided herein comprise 20% (w/w) hop alpha acids and 0.25% (w/v) myristic acid, 20% (w/w) hop alpha acids and 0.5% (w/v) myristic acid, 20% (w/w) hop alpha acids and 1% (w/v) myristic acid, 20% (w/w) hop alpha acids and 2.5% (w/v) myristic acid, 20% (w/w) hop alpha acids and 4% (w/v) myristic acid, 20% (w/w) hop alpha acids and 5% (w/v) myristic acid, or 20% (w/w) hop alpha acids and 10% (w/v) myristic acid.

In certain embodiments, the compositions provided herein further comprise hop beta acids.

In some embodiments, the compositions provided herein have a pH between about 8 and about 12 at 60° C. In some embodiments, the pH is between about 10 and about 12 at 60° C. In some embodiments, the compositions provided herein have a pH between about 8 and about 13 at room temperature. In certain embodiments, the pH is between about 8 and about 13 at a temperature of about 20° C. to about 26° C. In some embodiments, the pH is between about 10 and about 13 at a temperature of about 25° C. In some embodiments, the pH is about 10.5 at a temperature between about 20° C. and about 26° C.

In some embodiments, the compositions provided herein do not form a precipitate when cooled to 2° C. In certain embodiments, the compositions provided herein do not form precipitates when cooled to −12° C. or −16° C. and warmed back up to room temperature. In some embodiments, the compositions provided herein do not form a precipitate when cooled to −9° C. and warmed back up to room temperature. These compositions regain their initial properties when warmed to room temperature. In further embodiments, a resin precipitates is formed when the composition is cooled to −12° C. or −16° C. and resolubilizes when the composition is warmed to 20° C. and gently mixed. In all previous embodiments, the formulations described herein are warmed up to room temperature (without heating) with gentle shaking with "hand" if needed and no sonication. Once warmed up to room temperature, physical properties are observed (separation of resin formation, crystal formation or still a homogenous solution).

In some embodiments, the composition comprises 10% (w/w) alpha acids and 1% or more (w/v) myristic acid. These compositions do not form a precipitate when cooled to −12° C. In some embodiments, the composition comprises 10% (w/w) alpha acids and between 0.1% and 1% (w/v) myristic acid. These compositions form some precipitate when cooled to −8° C., and the precipitate resolubilizes when the composition is warmed to room temperature.

In some embodiments, the composition comprises about 15% (w/w) alpha acids and between 0.05% and 0.2% (w/v) myristic acid. These compositions do not form a precipitate when cooled to −8° C. These compositions form precipitate when cooled to 12° C. or below and warmed to room temperature. In some embodiments, the composition comprises about 15% (w/w) alpha acids and between 0.3% and 0.4% (w/v) myristic acid. These compositions do not form a precipitate when cooled to −12° C. In further embodiments, the composition comprises about 15% (w/w) alpha acids and between 0.3% and 0.4% (w/v) myristic acid. These compositions do not form a precipitate when cooled to −16.7° C. and warmed to room temperature.

The present disclosure further provides methods of controlling, preventing, and/or reducing bacterial growth in for example, an ethanol production process. In some embodiments, the method comprises adding a composition comprising hop alpha acids, myristic acid, and water to a fermentation vessel, a yeast propagation tank, or both. In a further embodiment, the method comprises adding an effective amount of aqueous solution of the compositions disclosed herein to a process medium. The pH of the process medium may range from about 2 to about 6. In certain embodiments, the method may comprise adding the compositions disclosed herein to the process medium continuously or discontinuously, e.g., using shock dosage. For example, for shock dosage, the composition is periodically added to the process medium, e.g., the dosage is made at defined times within very short time intervals at which locally and for a short time interval high concentrations can be adapted. The high local concentrations achieved by this kind of dosing avoid the adaptation of the micro-organisms. The compositions disclosed herein may be manually dosed into the process medium. Alternatively, the solution may be added to the process medium through closed dosing systems. That means that control of micro-organisms may be done under the use of the process installations (closed dosing systems) already available.

The method for controlling micro-organisms can be automated by the use of time controls for the dosing pumps and valves. The improved effect means that the overall concentration of active ingredients can be reduced, which produces a number of advantages. Either reduced costs are achieved through lower dosing or the same dosing produces a better effect.

The method for controlling micro-organisms using the compositions disclosed herein may be applied in an advantageous way in distilleries for the production of alcoholic drinks, specifically of spirits or in the production process of wine and wine containing drinks, further in the production of natural ethanol, fuel ethanol, sugar industry, and pharmaceutical drugs. The methods disclosed herein may also be used in the production of all kinds of dairy products, yeast, fruit juices, and tinned foods in aqueous solution. Furthermore, the methods may be used in the formulation of cosmetic and detergent compositions.

In certain embodiments, the disclosure provides a kit for reducing or preventing the growth of microorganisms comprising the compositions disclosed herein in a form suitable for delivery to a target site. In some embodiments, the target site is a fermentation vessel, a yeast propagation tank, or both. In certain embodiment, the target site is a heat exchanger, a liquefaction tank, or a seed tank.

EXAMPLES

Example 1

Figure 2:
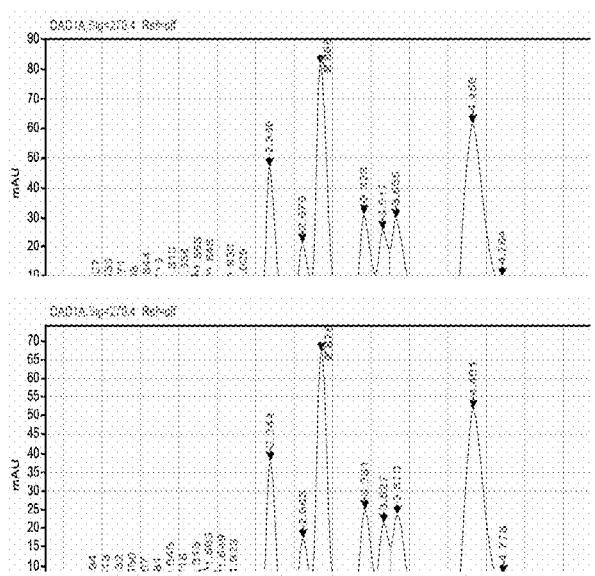
FIG. 2 depicts chromatograms of a 10% hop alpha acid formulation with 1% (w/v) myristic acid before (top panel) and after (bottom panel) freezing at −16.7° C. Both chromatograms were generated using an Agilent 1220 high-performance liquid chromatograph with the following parameters. Mobile phase: MeOH-Water 79%, $H_3PO_4$ 1%, EDTA 0.001%, flow 1.5, injection 10 µl.

Production of a 10% (W/W) Hop Alpha Acids Formulation with 1% (W/V) Myristic Acid A compound comprising 10% (w/w) alpha acids and 1% (w/v) myristic acid was formulated as follows. 100 ml of alpha acids containing 50% hexa-hydro-iso-alpha acids (HHIAA) and 50% tetra-hydro-iso-alpha acids (THIAA) was heated to 60° C. To this solution was added 1.0109 g of myristic acid at 60° C. The pH of this suspension was adjusted to 10.71 using KOH. The solution was cooled to room temperature using an ice water bath, and the pH was measured to be 11.67. The concentration of hop alpha acids was determined by high performance liquid chromatography (HPLC), and measured to be 5% (w/w) hexa-hydro-iso-alpha acids and 4% (w/w) tetra-hydro-iso-alpha acids (see FIG. 2, top panel).

Example 2

Figure 3:
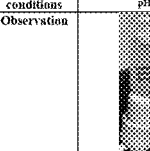
FIG. 3 depicts the results of cooling and rewarming several different 10% (w/w) hop alpha acids formulations. A formulation of hop alpha acids having pH 8.31 is shown in column two, a formulation of hop alpha acids having pH 11.58 is shown in column three, and a formulation of hop alpha acids and 1% myristic acid having pH 11.67 is shown in column four.

Comparison of Properties of 10% (W/W) Hop Alpha Acids Formulations with or without Myristic Acid An alpha acid composition comprising about 10% (w/w) alpha acids and having pH of 8.31 at was cooled to 3° C. for 24 hours. A resin precipitate was apparent following this treatment. See FIG. 3, second column. An alpha acid composition comprising about 10% (w/w) alpha acids (having pH of 11.58 at room temperature) was cooled to 0° C. for 24 hours. A suspended precipitate was apparent following this treatment. See FIG. 3, third column, top image. A second sample of the same composition was cooled to −2° C. for 24 hours. A resin precipitate was apparent following this treatment. See FIG. 3, third column, bottom image. Another alpha derived composition comprising about 10% (w/w) alpha acids and (1% (w/v) myristic acid and having a pH of 11.67 was cooled to −12° C. No precipitate was observed to form following this treatment. See FIG. 3, fourth column.

Example 3

Comparison of Properties of 9% (W/W) Hop Beta Acids Formulations and 10% (W/W) Hop Alpha Acids Formulations with Varying Amounts of Myristic Acid A beta acid composition comprising about 9% (w/w) beta acids and about 10% (w/v) myristic acid and having a pH of 12.03 at room temperature was cooled to −2° C. for 24 hours. At −2° C., the composition was observed to form a precipitate and crystals. See FIG. 1A, second column.

Alpha acid compositions comprising about 10% (w/w) alpha acids were also tested. A composition having a pH of 9.94 was cooled to −2° C. for 24 hours. At −2 C, the composition formed a resin precipitate. After re-warming to room temperature, the resin precipitate persisted. See FIG. 1A, third column. Similar results were obtained for an alpha acid composition having a pH of 12.37 at room temperature. See FIG. 1A, fourth column.

Figure 1B:
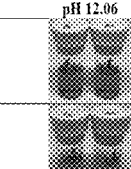
Figure 1B:
Figure 1B:
Figure 1B:

Alpha acid compositions comprising about 10% (w/w) alpha acids and varying amounts of myristic acid were then tested. The alpha acid composition comprising 10% (w/v) myristic acid and having a pH of 12.73 was cooled to −2° C. for 24 hours. At −2° C., resin or oil formation was not observed. See FIG. 1B, third column. An alpha acid composition comprising 5% (w/v) myristic acid and having a pH of 12.06 was cooled to −2° C. for 24 hours and no precipitate or oil formation was observed. See FIG. 1B, second column.

Example 4

Figure 4:
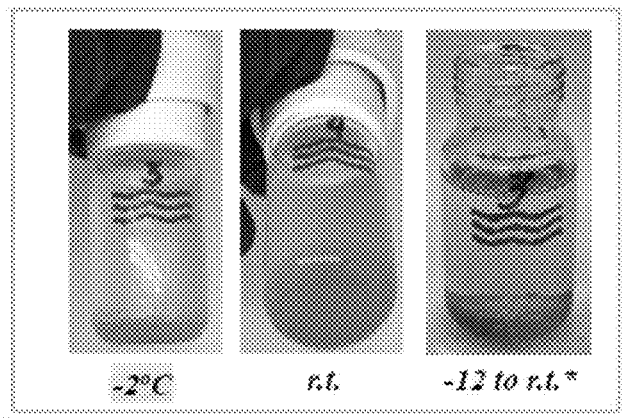
FIG. 4 depicts samples of a 10% (w/w) hop alpha acids formulation without myristic acid at different temperatures. The left image shows the formulation at −2° C., the center image shows the formulation at room temperature, and the right image shows the formulation after cooling to −12° C., rewarming to room temperature, and mixing.

Comparison of Properties of 10% (W/W) Hop Alpha Acids Formulations with Varying Amounts of Myristic Acid Alpha acid compositions with or without myristic acid were tested. An alpha hop acid composition comprising about 10% (w/w) alpha acids and no myristic acid was cooled to −2° C., which resulted in the formation of a resin precipitate. When the same formulation was cooled to −12° C. and re-warmed to room temperature with mixing, the precipitate persisted. See FIG. 4.

When myristic acid was added to an alpha acid hop composition, the composition could be cooled to a lower temperature without triggering the formation of a precipitate. An alpha hop acid composition comprising about 10% (w/w) alpha acids and about 1% (w/v) myristic acid having a pH of 11.9 could be cooled to −16.7° C. without formation of a precipitate. An alpha hop acid composition comprising about 10% (w/w) alpha acids and about 0.5% (w/v) myristic acid having a pH of 11.35 could be cooled to −9° C. without formation of a precipitate. An alpha hop composition comprising about 10% (w/w) alpha acids and about 0.25% (w/v) myristic acid having a pH of 11.3 could be cooled to −5° C. without formation of a precipitate.

Example 5

Figure 5:
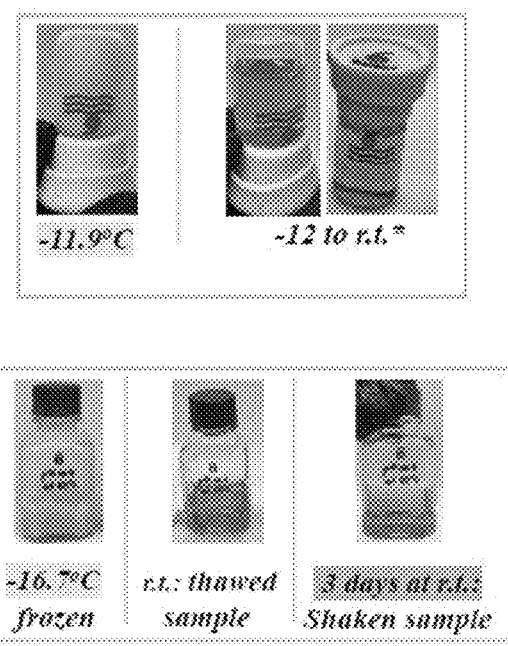
FIG. 5 depicts samples of a 10% (w/w) hop alpha acids formulation with 1% myristic acid at different temperatures. The top panel shows the formulation at −11.9° C. (left image) and after cooling to −12° C. and rewarming to room temperature (center and right images). The bottom panel shows the formulation at −16.7° C. (left image), after cooling to −16.7° C. and rewarming to room temperature (center image), and after cooling to −16.7° C., rewarming to room temperature, shaking, and standing at room temperature for three days (right panel).

Comparison of Properties of 10% (W/W) Hop Alpha Acids Formulations with or without Myristic Acid An alpha hop acid composition with about 10% (w/w) alpha acids having a pH of 8.31 at room temperature was observed to form a precipitate upon cooling to 2° C. An alpha hop acid composition with about 10% (w/w) alpha acids having a pH of 10.7 at room temperature was observed to form a precipitate upon cooling to −1° C. However, an alpha hop acid composition with about 10% (w/w) alpha acids and about 1% (w/v) myristic acid having a pH of 10.7 at room temperature could be cooled to −12° C. without formation of a precipitate. Upon re-warming of the composition to room temperature with gentle mixing, the composition regained its original properties. See FIG. 5, top panel. When the same composition was cooled to −16.7° C. and re-warmed to room temperature with gentle mixing, the composition regained its original properties and these properties, including a lack of precipitate, were maintained when the compositions was kept at room temperature for three days. See FIG. 5, bottom panel.

Example 6

Figure 6A:
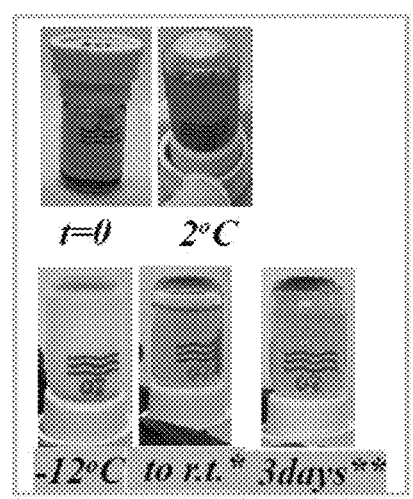
FIGS. 6A, 6B, and 6C depict samples of a 20% (w/w) hop alpha acids formulation with varied amounts of myristic acid at different temperatures.
Figure 6B:
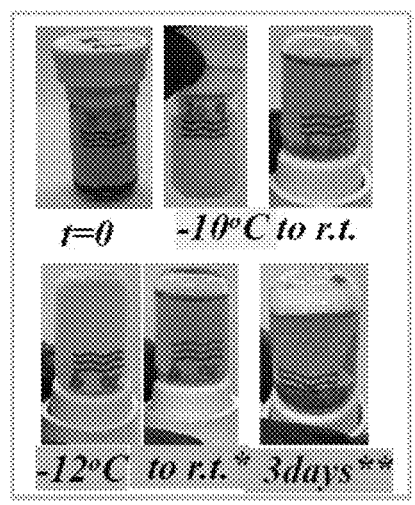
Figure 6C:
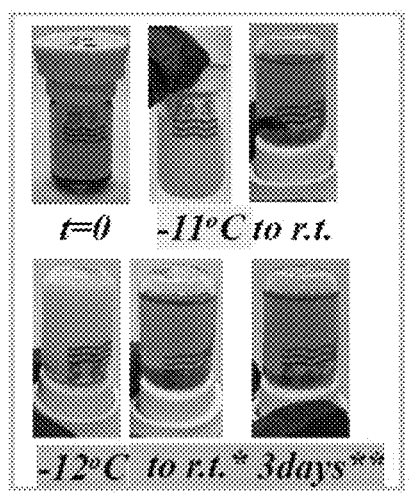

Comparison of Properties of 20% (W/W) Hop Alpha Acids Formulations with Varying Amounts of Myristic Acid An alpha hop acid composition with about 20% (w/w) alpha acids having a pH of 10.85 at 25° C. was cooled to 2° C. without formation of a precipitate. See FIG. 6A, top panel. When the same formulation was cooled to −12° C. and re-warmed to room temperature with gentle mixing, a large quantity of resin precipitate formed. The resin precipitate remained after three days at room temperature. See FIG. 6A, bottom panel. An alpha hop acid composition with about 20% (w/w) alpha acids and about 4% (w/v) myristic acid having a pH of 10.88 at 21.7° C. was cooled to −10° C. and re-warmed to room temperature. A small amount of resin precipitate was observed. See FIG. 6B, top panel. When the same formulation was cooled to −12° C. and re-warmed to room temperature with gentle mixing, a small amount of resin precipitate was observed. A portion of the precipitate remained after three days at room temperature. See FIG. 6B, bottom panel. An alpha hop acid composition with about 20% (w/w) alpha acids and about 5% (w/v) myristic acid was cooled to −11° C. and re-warmed to room temperature. No resin precipitate was observed. See FIG. 6C, top panel. When the same formulation was cooled to −12° C. and re-warmed to room temperature with gentle mixing, no resin precipitate was observed, and the lack of precipitate persisted after three days at room temperature. See FIG. 6C, bottom panel.

Example 7

Preparation of Hop Alpha Acids Formulations with Various Amounts of Myristic Acid (0.5% to 1.5% Ma)

The general procedure for the preparation of hop derived alpha acids formulations comprising myristic acids (MA) was as follows: Hop alpha acid formulation comprising 17.36% Hop Acid liquid (pH 9.95 at 28° C. and, 8.54 at 57.8° C.) was heated up to 60° C. and a determined mass of myristic acid (MA) ranging from 0.5, 0.75, 1, 1.25, and 1.5% w/v, was added. The amount of KOH added was stoichiometrically proportional to the content of MA. At this point, the pH of the mixture increases to range 10.0-10.2 at 60° C. and then stabilized following stirring for 15 min. Then, the solution was cooled down to room temperature (r.t.) using an ice bath (pH range 10.4-10.7). The concentration of alpha acids was determined using HPLC.

The Specific Formulations with Varying Amounts of MA were Prepared as Follows:

To prepare a formulation of hop derived alpha acids comprising 0.5% MA: 0.2498 g of MA was added to 15.74% total reduced hop acids at 60° C. Then, 1.43 eq, of KOH 40% was added dropwise to the emulsion. After adding the base the pH increased to 10.04 at 59° C. and the mixture pH stabilised after stirring for 10 min. The solution was cooled down to room using an ice bath. The pH of the solution at r.t. was determined to be 10.53. The concentration of alpha acids was determined to be [% HHIAA]=15.14: [% THIAA]=0.6, total alpha acids=15.74%.

To prepare a formulation of hop derived alpha acids comprising 0.75% MA, 0.3752 g of MA was added to 16.69% total reduced hop alpha acids at 60° C. (pH 8.54 at 58° C.). Then, 1.3 eq, of KOH 40% was added dropwise to the emulsion. After adding the base the pH increased to 10.00 at 57.2° C. and the mixture pH stabilised after stirring for 10 minutes. The solution was cooled down to r.t. using an ice bath and the pH of the solution at r.t. was determined to be 10.4. The concentration of alpha acids was determined to be [% HHIAA]=16.05: [% THIAA]=0.64, total alpha acids=16.69%.

To prepare a formulation of hop derived alpha acids comprising 1% MA: 0.5003 g of MA was added to 15.62% total reduced hop alpha acids at 60° C. (pH 8.54 at 58° C.). Then, 1.24 eq, of KOH 40% was added dropwise to the emulsion. After adding the base the pH increased to 10.09 at 58.2° C. and the mixture pH stabilised after stirring for 10 min. The solution was cooled down to r.t. using an ice bath and the pH of the solution was determined to be 10.53. The concentration of alpha acids was determined to be [% HHIAA]=15.0: [% THIAA]=0.61, total alpha acids=15.62%.

To prepare a formulation of hop derived alpha acids comprising 1.25% MA: 0.625 g of MA was added to 16.89% total reduced hop alpha acids at 60° C. (pH 8.54 at 58° C.). Then, 1.16 eq, of KOH 40% was added dropwise to the emulsion. After adding the base the pH increased to 10.03 at 57.3° C. and the mixture pH stabilised after stirring for 10 min. The solution was cooled down to r.t. using an ice bath and the pH of the solution was determined to be 10.41. The concentration of alpha acids was determined to be [% HHIAA]=16.23: [% THIAA]=0.66, total alpha acids=16.89%.

To prepare a formulation of hop derived alpha acids comprising 1.5% MA: 0.7503 g of MA was added to 17.47% total reduced hop alpha acids at 60° C. (pH 8.54 at 58° C.). Then, 1.15 eq, of KOH 40% was added dropwise to the emulsion. After adding the base the pH increased to 10.00 at 57.7° C. and the mixture pH stabilised after stirring for 10 min. The solution was cooled down to r.t. using an ice bath and the pH of the solution was determined to be 10.54. The concentration of alpha acids was determined to be [% HHIAA]=16.75: [% THIAA]=0.72, total alpha acids=17.47%.

Example 8

Stability Study for a Temperature Range from 5 to −12° C. for Formulations of Hop Alpha Acids with Various Amounts of Myristic Acid (0.5 to 1.5% (w/v)) Ma The formulated products were tested at appropriate low temperatures ranging from 5° C. to −12° C. to determine their chemical and physical properties. The temperature was dropped from 5° C. down to −12° C. in one-degree increments for 24 hrs each degree. Following which, the samples were warmed up to room temperature (without heating) with gentle shaking with "hand" if needed, and no sonication. Once warmed up to room temperature (r.t.), physical properties of the samples were observed (separation of resin formation, crystal formation or a homogenous solution). The determination of Hop α and β acids in Hop acid products in the samples exposed to low temperatures was performed using high-performance liquid chromatography (HPLC).

An improvement in the tolerance, of hop derived alpha acids formulations comprising myristic acid (MA) in percentages weight (g) per volume (100 mL) as an emulsifier, to low-temperature changes, was observed (FIGS. 7B-7F). The formulations of alpha acids comprising MA (0.5% to 1.5% w/v) could be frozen below the limit of −9° C. without display of any resin precipitation. These formulations recovered their initial properties after reaching a room temperature (r.t., see Table 1 and FIGS. 7B-7F) with the cooling recirculation system turned off. The improvement is significant because the hop alpha acid formulations comprising MA do not display any resin precipitation after thawing and warming up to r.t. These studies have determined that MA above 0.5% increased the tolerance of hop alpha acids to low temperatures with complete stability until −12° C., avoiding the resin precipitation in the range of pH 10.4-10.7 at r.t.

Figure 7A:
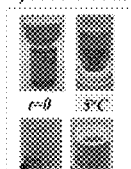
FIGS. 7A, 7B, 7C, 7D, 7E, and 7F shows the results of cooling and rewarming of formulation of hop alpha acids without MA (control)(FIG. 7A) and formulations of hop alpha acids comprising MA in an amount of 0.5% (FIG. 7B), 0.75% (FIG. 7C), 1% (FIG. 7D), 1.25% (FIG. 7D), and 1.5% (FIG. 7F) w/v (g/100 mL). All formulations were cooled down to −12° C. and rewarmed to room temperature with gentle mixing. Bottom panel for each figure shows formulations rewarmed to room temperature from −12° C.
Figure 7B:
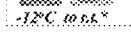
Figure 7C:
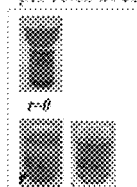
Figure 7D:
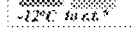
Figure 7E:
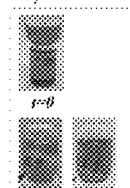
Figure 7F:
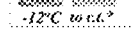
Figure 8A:
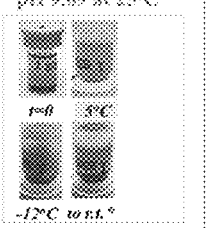
(FIG. 8A, bottom panel), before being rewarmed to room temperature. Hop acids formulations comprising 0.05% and 0.1% (w/v) of MA were first cooled to −9° C. before being rewarmed to room temperature.
Figure 8B:
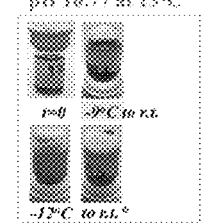
FIGS. 8B, 8C, 8D, 8E, and 8F shows the results of cooling and rewarming of formulation of hop alpha acids without MA (control) (FIG. 8A), and formulations of hop alpha acids comprising MA in an amount of 0.05% (FIG. 8B), 0.1% (FIG. 8C), 0.2% (FIG. 8D), 0.3% (FIG. 8E) and 0.4% (FIG. 8F) w/v (g/100 mL), cooled down to −9° C. and −12° C. before being rewarmed to room temperature. Control Hop acids formulation (FIG. 8A, top row) was first cooled to 5° C. and then to −12° C.
Figure 8C:
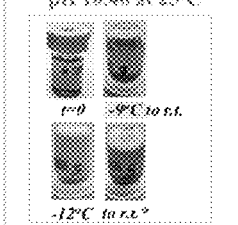
Figure 8D:
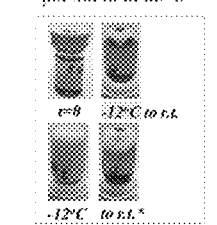
Figure 8E:
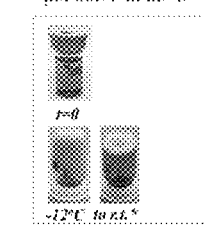
Figure 8F:
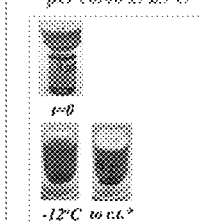

In comparison, hop derived alpha acid formulations without MA (control formulation) precipitate after reaching the temperature of 5° C. (FIG. 7A). Further, it was observed that the control formulation is unable to recover its initial characteristics after reaching room temperature: [% HHIAA]=5.59: [% THIAA]=17.91 Total alpha acids=6.12%.

the mixture increased to 10.11 at 57.9° C. The solution was cooled down to r.t. using an ice bath. The pH of the solution was determined to be 10.51. The concentration of alpha acids was determined to be [% HHIAA]=15.4: [% THIAA]=0.52, total alpha acids=15.92%.

To prepare a formulation of hop derived alpha acids comprising 0.2% MA: 0.15 g of MA was added to 15.99% total reduced hop alpha acids at 60° C. (pH 8.74 at 58.7° C.). Then, 1.73 eq, of KOH 40% was added dropwise to the

TABLE 1

Concentration after thawing study from −12° C. to r.t (*The Temperature of the bath and analyte** were 15.7° C. after turn off the system by 15 h).

| Sample name | Control Hop derived Alpha Acid Extract | Hop derived Alpha Acid Extract 0.5% MA | Hop derived Alpha Acid Extract 0.75% MA | Hop Derived Alpha Acid Extract 1% MA | Hop Derived Alpha Acid Extract 1.25% | Hop Derived Alpha Acid Extract 1.5% MA |
|---|---|---|---|---|---|---|
| t = initial HPLC analysis | [% HHIAA] = 16.64:[% THIAA] = 0.67, Total α acids = 17.31%. | [% HHIAA] = 15.14:[% THIAA] = 0.6, Total α acids = 15.74%. | [% HHIAA] = 16.05:[% THIAA] = 0.64, Total α acids = 16.69%. | [% HHIAA] = 15.0:[% THIAA] = 0.61, Total α acids = 15.62% | [% HHIAA] = 16.23:[% THIAA] = 0.66, Total α acids = 16.89%. | [% HHIAA] = 16.75:[% THIAA] = 0.72, Total α acids = 17.47%. |
| t = final HPLC analysis | [% HHIAA] = 15.71:[% THIAA] = 0.55, Total α acids = 16.25%. pH 9.46 at rt | [% HHIAA] = 16.12:[% THIAA] = 0.56, Total α acids = 16.68%. pH 10.52 at rt | [% HHIAA] = 16.12:[% THIAA] = 0.55, Total α acids = 16.62%. pH 10.34 at rt | [% HHIAA] = 15.84:[% THIAA] = 0.54, Total α acids = 16.37%. pH 10.4 at rt | [% HHIAA] = 15.91:[% THIAA] = 0.54, Total α acids = 16.45%. pH 10.31 at rt | [% HHIAA] = 15.67:[% THIAA] = 0.54, Total α acids = 16.21%. pH 10.49 at rt |
| Final observation | Resin remaining precipitated. | Stable formulation. | Stable formulation. | Stable formulation. | Stable formulation. | Stable formulation. |

**The samples were only shaken (not heated up for homogenization) and sampling at 15.7° C.

Example 9

Production of Hop Derived Alpha Acids Formulations with Various Amounts of Myristic Acid (0.05% to 0.4% Ma w/v)

The general procedure for the preparation of the hop derived alpha acid formulations comprising 0.05% to 0.4% MA w/v, subjected to stability testing was as follows: Hop alpha acids 15.8% HHIAA:THIAA liquid (pH 9.95 at 28° C. and, 8.54 at 57.8° C.) was heated up to 60° C. and to it was added a determined mass of myristic acid ranging from 0.05, 0.1, 0.2, 0.3, and 0.4% w/v (the percentage amount of MA was calculated as weight (g) per volume (100 mL). At this point, the pH of the mixture increases to range 10.0-10.2. Then, the solution was cooled down to r.t. using an ice bath. The concentration of HHIAA and THIAA was determined using HPLC.

The Specific Formulations with Varying Amounts of MA were Prepared as Follows:

To prepare a formulation of hop derived alpha acids comprising 0.05% MA: 0.0375 g of MA was added to 15.8% total reduced hop alpha acids at 60° C. (pH 8.74 at 58.7° C.). Then, 4.34 eq, of KOH 40% was added dropwise to the emulsion. Following addition of the base, the pH of the mixture increased to 10.08 at 59.4° C. and then stabilized after stirring for 10 min. The solution was cooled down to r.t. using an ice bath. The pH of the solution was determined to be 10.77. The concentration of alpha acids was determined to be [% HHIAA]=15.37: [% THIAA]=0.5, total alpha acids=15.87%.

To prepare a formulation of hop derived alpha acids comprising 0.1% MA: 0.00033 mmol of MA added to 15.92% total reduced hop alpha acids at 60° C. (pH 8.74 at 58.7° C.). Then, 2.61 eq of KOH 40% was added dropwise to the emulsion. Following addition of the base, the pH of emulsion. Following addition of the base, the pH of the mixture increased to 10.11 at 58.7° C. The solution was cooled down to r.t using an ice bath. The pH of the solution was determined to be 10.48. The concentration of alpha acids was determined to be [% HHIAA]=15.47: [% THIAA]=0.52, total alpha acids=15.99.

To prepare a formulation of hop derived alpha acids comprising 0.3% MA: 0.225 g of MA was added to 16.02% total reduced hop alpha acids at 60° C. (pH 8.74 at 58.7° C.). Then, 1.8 eq, of KOH 40% was added dropwise to the emulsion. Following addition of the base, the pH of the mixture increased to 10.03 at 59.5° C. The solution was cooled down to r.t. using an ice bath. The pH of the solution was determined to be 10.71. The concentration of alpha acids was determined to be [% HHIAA]=15.5: [% THIAA]=0.52, total alpha acids=16.02%.

To prepare a formulation of hop derived alpha acids comprising 0.4% MA: 0.3009 g, of MA (pH 7.82 at 53° C.) was added to 15.89% total reduced hop a acids at 60° C. (pH 8.74 at 58.7° C.). Then, 1.63 eq, of KOH 40% was added dropwise to the emulsion. Following addition of the base, the pH of the mixture increased to 10.08 at 58.3° C. The solution was cooled down to r.t. using an ice bath. The pH of the solution was determined to be pH 10.46 at r.t. The concentration of alpha acids was determined to be [% HHIAA]=15.39: [% THIAA]=0.5, total alpha acids=15.89%.

Example 10

Freezing Stability Study 5 to −12° C. for Formulations of Hop Derived Alpha Acids with Various Amounts of Myristic Acid (0.05 to 0.4%) Ma The formulated products were tested at appropriate low temperatures ranging from 5° C. to −12° C. to determine their chemical and physical properties. The temperature was dropped from 5° C. down to −12° C. in one-degree increments for 24 hrs each degree. Following which, the samples were warmed up to room temperature (without heating) with gentle shaking with "hand" if needed and no sonication. Once warmed up to room temperature (r.t.), physical properties of the samples were observed (separation of resin formation, crystal formation or a homogenous solution). The determination of Hop alpha (Hop α) and beta (Hop β) acids in Hop acid products in the samples exposed to low temperatures was performed using high-performance liquid chromatography (HPLC).

The present assay describes the stability of hop derived alpha acids formulations below 0.5% MA as percent w/v (g/100 mL). FIGS. 8A-8F and Table 2 summarize the most representative changes between a temperature range of 5° C. to −12° C. for 24 hrs each degree. We have observed two sub-formulation ranges 0.05 to 0.2% MA that confers low temperature tolerance to alpha hop acid solution down to −8° C. The same formulations displayed some cloudiness or minor resin precipitation after reaching −9° C. Resin precipitant in this range of formulations at −12° C. to r.t. (FIGS. 8A-8F) was observed. The next formulation range between 0.3 and 0.4% MA provides an excellent tolerance to low temperatures since the samples can be frozen in the temperature range of −10° C. to −12° C. but does not display any resin precipitation and the sample recovered its initial properties (see FIGS. 8E-8F, table 2).

Example 11

Hop Alpha Acids with Myristic Acid (Ma; 0.05, 0.1, 0.2, 0.3, 0.4% W/V), Freezing Study at −16.7° C.

The formulated products were tested at appropriate low temperatures ranging from 5° C. to −12° C. to determine their chemical and physical properties. The temperature was dropped down to −16.7° C. in one-degree increments for 24 hrs each degree. Following which, the samples were warmed up to room temperature (without heating) with gentle shaking with "hand" if needed and no sonication. Once warmed up to room temperature (r.t.), physical properties of the samples were observed (separation of resin formation, crystal formation or a homogenous solution). The determination of Hop α and β acids in Hop acid products in the samples exposed to low temperatures was performed using high-performance liquid chromatography (HPLC).

Figure 9A:
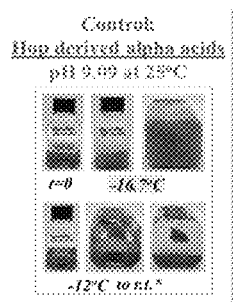
FIGS. 9B, 9C, 9D, 9E, and 9F shows the results of cooling and rewarming of formulation of hop alpha acids without MA (Control) (FIG. 9A), and formulations of hop alpha acids comprising MA in an amount of 0.05% (FIG. 9B), 0.1% (FIG. 9C), 0.2% (FIG. 9D), 0.3% (FIG. 9E), and 0.4% (FIG. 9F) w/v (g/100 mL) cooled down to −16.7° C. before being rewarmed to room temperature. All samples were cooled to −16.7° C. and rewarmed to room temperature slowly with gentle mixing. Top panel for each formulation shows formulations cooled down to −16.7° C., and bottom panels for each formulation shows formulations rewarmed to room temperature from −12° C.
Figure 9B:
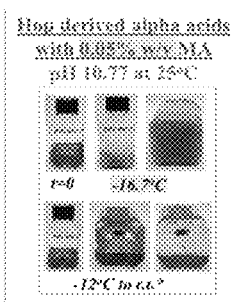
Figure 9C:
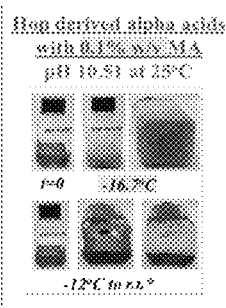
Figure 9D:
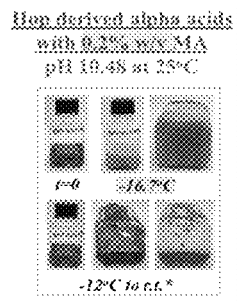
Figure 9E:
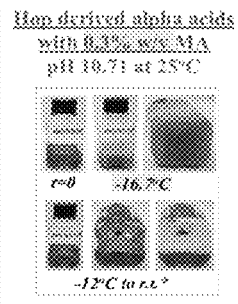
Figure 9F:
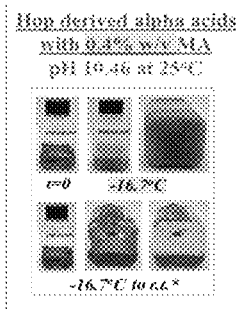

Samples between 0.05 to 0.2% display resin precipitation after thawing and mixing (FIGS. 9B-9D). The present data provide conclusive information to demonstrate that formulations of Hop alpha acid solution with 0.3 and 0.4% MA as emulsifier confer full protection to avoid any resin precipitation after the samples were frozen at −16.7° C. and subsequent thawing to r.t. (FIGS. 9E-9F and Table 3).

TABLE 2

Concentration after thawing study from −12° C. to r.t (*The Temperature of the bath and analyte were 12.8° C. after turn off the system by 15 h).

| Sample name: | Control Hop derived Alpha Acid Extract | Hop derived Alpha Acid Extract 0.05% MA | Hop derived Alpha Acid Extract 0.1% MA | Hop derived Alpha Acid Extract 0.2% MA | Hop derived Alpha Acid Extract 0.3% MA | Hop derived Alpha Acid Extract 0.4% MA |
|---|---|---|---|---|---|---|
| t = initial HPLC analysis | [% HHIAA] = 15.29:[% THIAA] = 0.51, Total α acids = 15.8%. pH 9.09 at 25° C. | [% HHIAA] = 15.37:[% THIAA] = 0.5, Total α acids = 15.87%. pH 10.77 at 25° C. | [% HHIAA] = 15.4:[% THIAA] = 0.52, Total α acids = 15.92%. pH 10.51 at 25° C. | [% HHIAA] = 15.47:[% THIAA] = 0.52, Total α acids = 15.99%. pH 10.48 at 25° C. | [% HHIAA] = 15.5:[% THIAA] = 0.52, Total α acids = 16.02%. pH 10.71 at 25° C. | [% HHIAA] = 15.39:[% THIAA] = 0.5, Total α acids = 15.89%. pH 10.46 at 25° C. |
| t = final HPLC analysis (at 12.8° C.) | [% HHIAA] = 14.57:[% THIAA] = 0.46, Total α acids = 15.03%. pH 9.12 at rt | [% HHIAA] = 15.24:[% THIAA] = 0.5, Total α acids = 15.74%. pH 10.10 at rt | [% HHIAA] = 15.13:[% THIAA] = 0.5, Total α acids = 15.63%. pH 10.10 at rt | [% HHIAA] = 15.05:[% THIAA] = 0.49, Total α acids = 15.91%. pH 10.07 at rt | [% HHIAA] = 15.87:[% THIAA] = 0.52, Total α acids = 16.39%. pH 10.2 at rt | [% HHIAA] = 15.26:[% THIAA] = 0.5, Total α acids = 15.68%. pH 10.02 at rt |
| Final Observation (at 12.8° C.) | The resin remains precipitated after thawing and mixing. | The resin remains precipitated after thawing and mixing. | The resin remains precipitated after thawing and mixing. | The resin remains precipitated after thawing and mixing. | Stable formulation: The frozen samples recovered the initial properties after thawing. | Stable formulation. |

**The samples were only shaken (not heat up for homogenization) and sampling at 12.8° C.

TABLE 3

Concentration after thawing study from −16.7° C. to r.t (23.7° C., Note: this is the temperature after 24 h).

| | Control Hop derived Alpha Acid Extract | Hop derived Alpha Acid Extract 0.05% MA | Hop derived Alpha Acid Extract 0.1% MA | Hop derived Alpha Acid Extract 0.2% MA | Hop derived Alpha Acid Extract 0.3% MA | Hop derived Alpha Acid Extract 0.4% MA |
|---|---|---|---|---|---|---|
| t = initial HPLC analysis | [% HHIAA] = 15.29:[% THIAA] = 0.51, Total α acids = 15.8%. pH 9.09 at rt | [% HHIAA] = 15.37:[% THIAA] = 0.5, Total α acids = 15.87%. pH 10.77 at rt | [% HHIAA] = 15.4:[% THIAA] = 0.52, Total α acids = 15.92%. pH 10.51 at rt | [% HHIAA] = 15.47:[% THIAA] = 0.52, Total α acids = 15.99%. pH 10.48 at rt | [% HHIAA] = 15.5:[% THIAA] = 0.52, Total α acids = 16.02%. pH 10.71 at rt | [% HHIAA] = 15.39:[% THIAA] = 0.5, Total α acids = 15.89%. pH 10.46 at rt |
| t = final HPLC analysis | [% HHIAA] = 14.87:[% THIAA] = 0.49, Total α acids = 15.36%. pH 9.34 at rt | [% HHIAA] = 16.24:[% THIAA] = 0.53, Total α acids = 16.77%. pH 10.44 at rt | [% HHIAA] = 15.01:[% THIAA] = 0.5, Total α acids = 15.51%. pH 10.29 at rt | [% HHIAA] = 15.39:[% THIAA] = 0.52, Total α acids = 15.91%. pH 10.69 at rt * | [% HHIAA] = 15.23:[% THIAA] = 0.53, Total α acids = 15.76%. pH 10.38 at rt | [% HHIAA] = 15.62:[% THIAA] = 0.52, Total α acids = 16.14%. pH 10.43 at rt |
| Final observation | Resin remaining precipitated | Resin remaining precipitated | Resin remaining precipitated | Resin remaining precipitated | Not changes. Stable formulation. | Not changes. Stable formulation. |

* No reduction. pH meter calibration (17 Jun. 2021) = 96.6%, offset − 26 mV.

It was determined that hop derived alpha acids formulations with levels above 0.3% w/v (g/100 mL) MA improve the tolerance to low-temperature exposure. These samples recovered their initial properties completely, even when thawed to 12.8° C. after 15 h. The formulation with 0.4% w/v MA does not display any physical alteration after exposure to the complete range of temperatures used in this study (5 to −12° C.).

On the other hand, hop derived alpha acids formulations with 0.3 to 0.4% w/v MA recovered their initial properties at 23.7° C. from −16.7° C. after 24 h and a soft mixing (no resin precipitation was observed).

Based on these data (1$^{st}$: Hop derived alpha acid extract with myristic acid (MA; 0.5, 0.75, 1, 1.25, 1.5% w/v), freezing study 5 to −12° C.; 2$^{nd}$: Hop derived alpha acid extract with myristic acid (MA; 0.05, 0.1, 0.2, 0.3, 0.4% w/v), freezing study 5 to −12° C.; and 3$^{rd}$: Hop derived alpha acid extract with myristic acid (MA; 0.05, 0.1, 0.2, 0.3, 0.4% w/v), freezing study at −16.7° C.), it was determined that 0.3 to 0.4% w/v (g/100 mL) MA is the optimal range that confers full protection to hop derived alpha acids extract at low temperatures without over-charging the composition with the emulsifier.

TABLE 4

Summary of the Freezing stability studies with different ranges of Myristic Acid:

| Sample name: Temperature (° C.) | Hop derived alpha acid Extract Control | Re-formulation percent of emulsifier (% w/v, g/100 mL of myristic acid) | | | | | | | | | |
|---|---|---|---|---|---|---|---|---|---|---|---|
| | | 0.05 | 0.1 | 0.2 | 0.3 | 0.4 | 0.5 | 0.75 | 1 | 1.25 | 1.5 |
| 5 | P | S | S | S | S | S | S | S | S | S | S |
| 4 | P | S | S | S | S | S | S | S | S | S | S |
| 3 | P | S | S | S | S | S | S | S | S | S | S |
| 2 | P | S | S | S | S | S | S | S | S | S | S |
| 1 | P | S | S | S | S | S | S | S | S | S | S |
| 0 | P | S | S | S | S | S | S | S | S | S | S |
| −1 | P | S | S | S | S | S | S | S | S | S | S |
| −2 | P | S | S | S | S | S | S | S | S | S | S |
| −3 | P | S | S | S | S | S | S | S | S | S | S |
| −4 | P | S | S | S | S | S | S | S | S | S | S |
| −5 | P | S | S | S | S | S | S | S | S | S | S |
| −6 | P | S | S | S | S | S | S | S | S | S | S |
| −7 | P | S | S | S | S | S | S | S | S | S | S |
| −8 | P, F, NRi | PSR, S | PSR, S | PSR, S | S | S | S | S | S | S | S |
| −9 | P, F, NRi | PF, PSR, Ri, NRi | PF, PSR, Ri, NRi | PF, S | PF, Ri, S | S | S | S | S | PF, Ri, S | S |
| −10 | P, F, NRi | PF, Ri, S | PF, Ri, S | PF, Ri, S | F, Ri, S | S | F, Ri, S | S | S | F, Ri, S | PF, Ri, S |
| −11 | P, F, NRi | F, Ri, S | F, Ri, S | F, Ri, S | S | S | S | S | PF, Ri, S | PF, Ri, S | PF, Ri, S |
| −12 | P, F, NRi | F, NRi, P | F, NRi, P | F, NRi, P | F, Ri, S | S | PF, Ri, S | PF, Ri, S | S | PF, Ri, S | PF, Ri, S |

TABLE 4-continued

Summary of the Freezing stability studies with different ranges of Myristic Acid:

| Sample name: Temperature (° C.) | Hop derived alpha acid Extract Control | Re-formulation percent of emulsifier (% w/v, g/100 mL of myristic acid) | | | | | | | | | |
|---|---|---|---|---|---|---|---|---|---|---|---|
| | | 0.05 | 0.1 | 0.2 | 0.3 | 0.4 | 0.5 | 0.75 | 1 | 1.25 | 1.5 |
| −16.7 | P, F, NRi | P, F, NRi | P, F, NRi | P, F, NRi | F, Ri, S | F, Ri, S | N/A | N/A | N/A | N/A | N/A |

Keywords:
S: Stable product,
P: Resin precipitation;
NP: No resin precipitation;
F: Frozen sample;
PF: Partially frozen sample;
Ri: Recovery of the initial properties;
NRi: Not recovery of the initial properties;
PSR: A possible sign of resin precipitation The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition comprising hop alpha acids in an amount from about 1% to about 30% (w/w), myristic acid in an amount from about 0.05% to about 15% (w/v), and water.

2. The composition of claim 1, wherein the hop alpha acids comprise hexa-hydro-iso-alpha acids and tetra-hydro-iso-alpha acids, and wherein the hexa-hydro-iso-alpha acids and tetra-hydro-iso-alpha acids are present in a ratio of about 1:1.

3. The composition of claim 1, wherein the hop alpha acids are present as potassium salts.

4. The composition of claim 1, wherein the hop alpha acids are present in an amount from about 10% to about 20% (w/w).

5. The composition of claim 1, wherein the myristic acid is present in an amount from (i) about 0.05% to about 2% (w/v), (ii) about 0.3% to about 1.5% (w/v), (iii) about 0.05% to about 0.25% (w/v), or (iv) about 0.3% to about 0.4% (w/v).

6. The composition of claim 1, wherein the myristic acid is present in an amount from about 0.25% to about 15% (w/v).

7. The composition of claim 6, wherein the myristic acid is present in an amount of about 0.25% (w/v), about 0.5% (w/v), about 1% (w/v), about 2.5% (w/v), about 5% (w/v), or about 10% (w/v).

8. The composition of claim 1, wherein the composition has a pH between about 8 and about 12 at 60° C., a pH between about 8 and about 13 at a temperature between about 20° C. and about 26° C., or a pH of about 10.5 at a temperature between about 20° C. and about 26° ° C.

9. The composition of claim 1, further comprising hop beta acids.

10. The composition of claim 1, wherein the composition does not form a precipitate when cooled to (i) about −2° C., (ii) about −12° C., or (iii) about −16° C.

11. A method of controlling bacterial growth in a process medium utilizing fermentation, the method comprising adding to the process medium a hop composition comprising:
(a) hop alpha acids in an amount from about 1% to about 30% (w/w);
(b) myristic acid in an amount from about 0.05% to about 15% (w/v); and
(c) water.

12. The method of claim 11, wherein the process utilizing fermentation is an ethanol production process, and wherein the hop composition is added to the process medium in a fermentation vessel, a yeast propagation tank, or both.

13. The method of claim 11, wherein the hop alpha acids comprise hexa-hydro-iso-alpha acids and tetra-hydro-iso-alpha acids, wherein the hexa-hydro-iso-alpha acids and tetra-hydro-iso-alpha acids are present in a ratio of about 1:1, and wherein the hop alpha acids are present as potassium salts.

14. The method of claim 11, wherein the hop alpha acids are present in an amount from about 10% to about 20% (w/w).

15. The method of claim 11, wherein the myristic acid is present in an amount from about 0.05% to about 2% (w/v), about 0.3% to about 1.5% (w/v), about 0.05% to about 0.25% (w/v), or about 0.3% to about 0.4% (w/v).

16. The method of claim 11, wherein the myristic acid is present in an amount from about 0.25% to about 15% (w/v).

17. The method of claim 11, wherein the composition has a pH between about 8 and about 12 at 60° C., a pH between about 8 and about 13 at a temperature between about 20° ° C. and about 26° C., or a pH of about 10.5 at a temperature between about 20° C. and about 26° C.

18. The method of claim 11, further comprising hop beta acids.

19. A kit for reducing or preventing the growth of microorganisms comprising: composition comprising:
(a) hop alpha acids in an amount from about 1% to about 30% (w/w);

(b) myristic acid in an amount from about 0.05% to about 15% (w/v); and
(c) water, wherein the composition is in a form suitable for delivery to a target site.

* * * * *